US009622970B2

(12) United States Patent
Liu

(10) Patent No.: US 9,622,970 B2
(45) Date of Patent: Apr. 18, 2017

(54) PHARMACEUTICAL COMPOSITION CONTAINING LUTEIN AND ANTIOXIDANT FOR TREATING AND PREVENTING HUMAN DISEASE

(71) Applicant: Yaguang Liu, Tuckerton, NJ (US)

(72) Inventor: Yaguang Liu, Tuckerton, NJ (US)

( * ) Notice: Subject to any disclaimer, the term of this patent is extended or adjusted under 35 U.S.C. 154(b) by 0 days.

(21) Appl. No.: 14/120,219

(22) Filed: May 8, 2014

(65) Prior Publication Data

US 2015/0320699 A1 Nov. 12, 2015

(51) Int. Cl.

| | |
|---|---|
| ***A61K 9/127*** | (2006.01) |
| ***A61K 31/047*** | (2006.01) |
| ***A61K 31/122*** | (2006.01) |
| ***A61K 9/00*** | (2006.01) |
| ***A61K 9/107*** | (2006.01) |
| ***A61K 47/42*** | (2017.01) |
| ***A61K 9/50*** | (2006.01) |

(52) U.S. Cl.

CPC ............ *A61K 9/127* (2013.01); *A61K 9/0053* (2013.01); *A61K 9/107* (2013.01); *A61K 9/1272* (2013.01); *A61K 9/5047* (2013.01); *A61K 9/5078* (2013.01); *A61K 31/047* (2013.01); *A61K 31/122* (2013.01); *A61K 47/42* (2013.01)

(58) Field of Classification Search

CPC .................................................... A61K 9/1075

See application file for complete search history.

(56) References Cited

U.S. PATENT DOCUMENTS 5,891,907 A * 4/1999 Kolter .................. A61K 9/1075 514/168
7,446,101 B1 * 11/2008 Madhavi .................. A61K 9/19 514/58
2004/0072800 A1 * 4/2004 Zhang ................. C08B 37/0015 514/58
2006/0240092 A1 * 10/2006 Breitenkamp ....... A61K 9/1075 424/450
2006/0286164 A1 * 12/2006 Iyer .......................... A61K 9/08 424/456
2008/0044475 A1 * 2/2008 Olvera ................ A61K 9/1075 424/488
2009/0311329 A1 * 12/2009 Livney ................ A23C 9/1322 424/489
2012/0288533 A1 * 11/2012 Livney .................. A23L 1/3002 424/400
2014/0099386 A1 * 4/2014 Montoya-Olvera . A61K 9/1075 424/638

OTHER PUBLICATIONS

Loftsson et al. (2002). "Self-Association and Cyclodextrin Solubilization of Drugs." Journal of Pharmaceutical Sciences, 91(11): 2307-2316.*
Tiwari et al. (2010). "Cyclodextrins in delivery systems: Applications." J Pharm Bioallied Sci, 2(2):72-79.*
Peng et al. "Astaxanthin Encapsulation by Mpeg-PCL Self-Assembled Polymeric Micelle." Presented at: 2015 AIChE Annual Meeting; Nov. 10, 2015; Salt Lake City, UT.*
Prospector. "2.0% Astaxanthin Vegetarian Beadlets." Retrieved from: https://www.ulprospector.com/en/na/Food/Detail/2252/66217/20-Astaxanthin-Vegetarian-Beadlets.*

* cited by examiner

*Primary Examiner* — Frederick Krass
*Assistant Examiner* — Amanda Heyes

(57) ABSTRACT

The present invention is to providing a new preparation including complex of a medical compound with lutein, astaxanthin and antioxidant. The new preparation includes stabilized liposome preparation, sustained release preparation and polymeric micelles preparation which used as delivery systems for lutein, astaxanthin and antioxidant. The new preparation significantly increases bioavailability of lutein and astaxanthin and uses for treatment and prevention of eyes and other disease.

1 Claim, No Drawings

PHARMACEUTICAL COMPOSITION CONTAINING LUTEIN AND ANTIOXIDANT FOR TREATING AND PREVENTING HUMAN DISEASE

BACKGROUND OF THE INVENTION

The present invention is to providing a new preparation including complex of a medical compound with lutein, astaxanthin and antioxidant. The new preparation includes stabilized liposome preparation, sustained release preparation and polymeric micelles preparation which used as delivery systems for lutein, astaxanthin and antioxidant. The new preparation significantly increases bioavailability of lutein and astaxanthin and uses for treatment and prevention of eyes and other disease.

DESCRIPTION OF THE PRIOR ART

Lutein and astaxanthin are important for human being. The human retina accumulates lutein and zeaxanthin. Lutein serves as a photo-protectant for retina from the damaging effects of free radicals produced by blue light. Lutein is present in plants as fatty-acid esters. It is isomeric with zeaxanthin, differing only in the placement of one double bond.

Lutein prevents vision loss and produced marked improvements in vision in people with active Age-Related Eye Disease (AMD), the more serious from of the disease.

An estimated 1.75 million Americans age 40 and older have age-related macular degeneration (AMD), a disease that gradually and stealthily destroys central vision. AMD is the leading cause of vision impairment and blindness in Americans 65 and older. More than seven million older people are at high risk for developing the condition. AMD begins with characteristic yellow deposits (drusen) in the macula. People with drusen can go on to develop advanced AMD. The risk is higher when the drusen are large and numerous and associated with disturbance in the pigmented cell layer under the macula. Large and soft drusen are related to elevated cholesterol deposits and may respond to cholesterol-lowering agents.

AMD is a medical condition which usually affects older adults and results in a loss of vision in the center of the visual field (the macula) because of damage to the retina. Macular degeneration can make it difficult or impossible to read or recognize faces. There is no cure so far.

Low plasma concentrations of lutein and zeaxanthin and an increased risk of developing AMD. Some studies support the view that supplemental lutein and/or zeaxanthin help protect against AMD. Lutein and zeaxanthin reduce the risk of AMD. Lutein was found to be concentrated in the macula, a small area of the retina responsible for central vision. It helps keep the eyes safe from oxidative stress and the high-energy photons of blue light.

Lutein is a lipophilic molecule and is generally insoluble in water. Therefore, lutein is difficultly to be absorbable by digestive system of human. The formulation of preparation of lutein is a key factor in lutein bioavailability.

The lutein market is segmented into pharmaceutical, nutraceutical food. The market is estimated to be about US$500 million. It is one of the faster growing areas of the US$27 billion antioxidant market.

The primary use for humans of astaxanthin is as a food supplement. Research shows that, due to astaxanthin's potent antioxidant activity, it may be beneficial in cardiovascular, immune, inflammatory and neurodegenerative diseases. Some research supports the assumption that it may protect body tissues from oxidative and ultraviolet damage through its suppression of NF-kB activation.

DETAILED DESCRIPTION OF THE INVENTION

Lutein is a lipophilic molecule and is generally insoluble in water. Therefore, lutein is difficulty to be absorbable by digestive system of human. Actually, only solubilized drug or health food molecules can be absorbed by the cellular membranes to subsequently reach the site of drug or health food action. Any drug or health food to be absorbed must be present in the form of an aqueous solution at the site of absorption. The capsules of lutein and astaxanthin, which selling as a health food, are difficult absorbable by human. Poor water soluble lutein and astaxanthin are allied with very slow and small drug absorption leading to inadequate bioavailability and gastrointestinal mucosal toxicity. Bioavailability depends on several factors, drug solubility in an aqueous environment and drug or health food permeability through lipophilic membranes being the important ones. The present invention is providing new preparation of lutein and astaxanthin, which can more soluble in gastrointestinal tract and let lutein and astaxanthin keep an effective level for prolonged time in blood.

The present invention is providing a new preparation for lutein or astaxanthin, such as liposome preparation, sustained release preparation and polymeric micelles preparation, and let lutein and astaxanthin have an effective level for prolonged time in blood. The present invention can make lutein and astaxanthin as a new preparation for easily abstract by human. The new preparation of lutein and astaxanthin can serve as medicine, health food, dietary supplements. In special lutein can serve as a photo-protectant for retina and skin from the damaging effects of free radicals produced by blue light.

Lutein is one of carotenoids and it is a lipophilic molecule. Carotenoids, in general, require the presence of fat for intestinal absorption, increasing the fat content of the diet twelve-fold has double the amount of lutein absorbance. If increasing so much fat at intestinal, it will cause big problems for human. For the reasons given above, absorption of lutein and astaxanthin are difficult for human.

The following specific examples will provide detailed illustrations of methods of producing new preparation of lutein and astaxanthin according to the present invention and pharmaceutical dosage units containing new preparation of lutein and astaxanthin. These examples are not intended, however, to limit or restrict the scope of the invention in any way, and should not be construed as providing conditions, parameters, reagents, or starting materials which must be utilized exclusively in order to practice the present invention.

Example 1

Preparation of Lutein-Containing Sterically Stabilized Liposomes

Hydrogenated phosphatidylcholine (PC), phosphatidylglycerol (PGL), and phosphatidylserine (PS) were extracted from soybean. All above lipids were finally purified on silicic acid columns, shown to be pure by thin-layer chromatography and stored in chloroform in sealed ampules under nitrogen until use. Phospholipids mixed with cholesterol (CHOL) and long-chain alcohol. The solvent was removed under reduced pressure by a rotory evaporator. Lipids were redissolved in the organic phase and reversed phase will be formed. Lutein-containing phosphate-buffered saline (Lutein was 3 mM in 0.1 M phosphate-buffered saline) was added at these lipid systems, and resulting two-phase system was sonicated 3 minutes until the mixture homogeneous that did not separate for at least two hours after sonicated. Lutein-SSL were sealed and sterilized. [$^3$H]-lutein and dialyzed method was used to determine the amount of encapsulated lutein. The size of the vesicles was determined by a dynamic light cattering technique. When PG/PC/CHOL were 1:4:5, diameter of liposomes was 20-50 nM (range). Lutein-SSL was very stabilized in at least six months.

So far, many articles reported drug-containing liposomes. However, in general, liposomes are not stabilized. In accordance with this invention, lutein-SSL is very stabilized in at least six months. Therefore lutein-SSL can be used in industry. Lutein-SSL can enhance and improve antioxidant activity of lutein. It is very important that all lipids are extracted from soybean. Therefore it is very safe for human being. Many articles reported lipids, which used for drug-containing liposomes, are syntheses by organic chemistry. However synthetic lipids have some side effects. The methods of preparing of lutein-SSL and phospholipids, which extracted from soybean, are very safe.

Example 2

New Sustained Release Preparation of Lutein

A. Methods of New Sustained Release Preparation 1 kg polyvinylpyrrolidone (PPD) (molecular weight 40.000) were dissolved in 10 liter of isopropand, and 1 kg of micronized lutein was dispersed in there. 3.5 kg of sugar was placed in suspension and mix. Lutein is coated onto the sugar seed by first combining it with a water soluble system such as polyethylene glycol or polyvinylpyrrolidone.

The resulting lutein coated sugar seeds are then coated with a pharmaceutically acceptable waterinsoluble system such as ethylcellulose, cellulose acetate butyrate or cellulose triacetate, with ethyl cellulose preferred. This coating enables release of the lutein. The average diameter of each of the finished micropellets is about 0.4 to 0.6 mm, preferably about 0.5 mm. This provides a coating with a sufficient amount of channels to enable the lutein to be released. The dissolution rate depends on the weight of the micropellets and solvent system. The pellets were screened.

As desired, the final coated products containing an ethylcellulose coating level of 1% was prepared. The pellets were dried under vacuum. The products contained 99.0% by weight of lutein and 1% by weight ethylcellulose coating.

B. Plasma Concentration of Lutein

Plasma concentration of lutein in rat was determined by regular methods.

TABLE 1

Plasma Concentration of lutein

| | Lutein | Sustained release of lutein |
|---|---|---|
| 1 h | 140 mg/ml | 90 mg/ml |
| 4 h | 100 mg/ml | 85 mg/ml |
| 8 h | 70 mg/ml | 70 mg/ml |
| 24 h | 30 mg/ml | 40 mg/ml |
| 48 h | 15 mg/ml | 30 mg/ml |
| 72 h | 8 mg/ml | 20 mg/ml |

The data in table shows that plasma concentration of lutein in sustained preparation was not significantly different from lutein in regular preparation before 8 hours. But it did after 8 hours. The data shows that bioavailability of sustained release preparation of lutein is better than regular lutein.

The formation of an inclusion complex of a medical compound with lutein in accordance with the process was detected by various methods such as powder X-ray diffraction, dissolution behavior, scanning electron microscope analysis, differential thermal analysis (DTA) and infrared absorption (IR). Inclusion complexes were prepared using lutein as a medical compound, and the behavior of dissolution and release of lutein from the inclusion complex in the capsule form, as well as the behavior of dissolution and release of lutein from compressed capsule containing the inclusion complex was determined.

The X-ray diffraction patterns support the fact that lutein and a pharmaceutical acceptable have complex with each other and formed an inclusion complex of them having a structure different from the original structures of the individual components.

The novelty of the present invention indicated in the mixture of the active ingredients with the specified proportions to produce lutein and in the preparation of dosage units are in pharmaceutically acceptable dosage form. The term “pharmaceutical acceptable dosage form” as used hereinabove includes any suitable vehicle for the administration of medications known in the pharmaceutical art, including, by way of example, tablets, capsules, syrups, and elixirs with specified ranges of lutein concentration.

Example 3

Preparation Polymeric Micelles-Lutein

An estimated 40% of approved drugs in the market and nearly 90% of molecules in the developmental pipeline are poorly water-soluble. The challenge to formulate insoluble drugs has met with advent of various insoluble drug formulation technologies. The polymers micelles with both hydrophobic and hydrophilic moiety in the chain can assemble into nano-sized micelles in water. Polymeric micelles solubilize is very important for poorly water-soluble compounds. A major factor in lutein solubilization is the compatibility of lutein and a core of a polymeric micelle. Polymeric micelles may circulate for prolonged periods in blood and gradually release lutein.

Polymeric micelles have gathered considerable attention in the field of lutein and gene delivery due to their excellent biocompatibility, low toxicity, enhanced blood circulation time, and ability to solubilize a large number of lutein in their micellar core. Polymeric micelles have emerged as important pharmaceutical carriers because of their attractive properties. Preparation of polymeric micelles appears to be relatively simple as compared with the other novel drug delivery systems. Polymeric micelles can be easily loaded with a wide variety of poorly soluble drugs, such as lutein, thus resulting in enhance bioavailability of lutein.

The method of Micelle Formation: 200 mg of copolymer were dissolved in 40 ml dimethyl acetamide and the polymer solution was transferred into a pre-swollen membrane and dialyzed against water for 24 h and subsequently lyophilized. The yield of the micelle formation was about 90%.

50 mg of micelle were solubilized by sonication for 40 min in water and stirred for another 3 h. The pH of the solution was adjusted by HCl to pH 2, kept for 14 h and readjusted to pH 7 by NaOH. The solution was again dialyzed against water for 24 h using a pre-swollen membrane to remove the salt and then frozen in liquid nitrogen and lyophilized, resulting in a yield of 90%.

Example 4

Using Natural Polymers for Self-Assembling

A. Natural Polymers:

Drug delivery plays an important role in the development of pharmaceutical dosage forms for the healthcare industry because often the duration of the drug release needs to be extended over a period of time. This can be achieved by the incorporation of drugs into polymeric materials to control drug release at a pre-defined and reproducible rate for a prolonged duration.

The majority of the drug delivery systems are fabricated from non-degradable polymers such as silicone, polyurethane and ethylene vinyl acetate copolymers. So far, the polymers were synthesized but chemical polymers have some side effects. Therefore we develop new natural biodegradable polymers. For example, soy polypeptide and polymers sodium Haidai are two natural polymers and they are an abundant, inexpensive and renewable-material.

Soy polypeptide (SPP) is isolated from soy protein, which content of 95% (dry basis), was obtained from special soybean (SSB). SSB is natural cultivated and it is not from a transfer-gene seeds. Also, SSBs are cultivated at no pollution area. Other natural biodegradable polymer is polysodium Haidai (PSH) which extracted from sea-plant Haidai. PSH is cream-colored powder. Molecular weight is about 240000. The major structure is linear polymer.

SPP/PSH is derived from renewable resource. Therefore, using SPP/PSH system has good environment value. SPP/PSH has been found good performance for the dehydration of ethanol/water mixture. SPP and SH are biodegradable, environmentally friendly, and readily available from an abundant renewable resource. It had been considered an important material for the development of new materials as devices for biotechnological and biomedical utilization.

B. Self-Assembling Properties

Self-assembling properties were examined by adding water to the liquid block copolymers (10% w/v). The mixture was stirred for 10 min. Micelle formation was determined at 25° C.

Measurement of lutein solubility in 10% w/v diblock copolymer micelles: The maximum lutein solubility in micelles was determined as follows: In a glass flask, 0.5 g of copolymer and 0.1 to 0.15 g of lutein was weighed and then mixed at 50° C. for 10 min using a magnetic stirrer followed by addition of 5 ml of filtered water (0.1 μm Millipore). The solution was stirred for 24 h at room temperature and then filtered through a 0.1 μm Millipore filter to remove non-solubilized lutein. A product was obtained using an ultraviolet (UV) spectrophotometer. Absorbances were measured at 260 nm at 233 nm. Solubility data are an average of at least three measurements.

The SPP/PSH systems are as agoodlutein carrier, polymer micelle possesses the following advantages: good stability, increasing solubility of insoluble drugs, release slowly, improving drug bioavailability.

Example 5

Preparation of Astaxanthin-Containing Sterically Stabilized Liposomes

Hydrogenated phosphatidylcholine (PC), phosphatidylglycerol (PGL), and phosphatidylserine (PS) were extracted from soybean. All above lipids were finally purified on silicic acid columns, shown to be pure by thin-layer chromatography and stored in chloroform in sealed ampules under nitrogen until use. Phospholipids mixed with cholesterol (CHOL) and long-chain alcohol. The solvent was removed under reduced pressure by a rotory evaporator. Lipids were redissolved in the organic phase and reversed phase will be formed. Astaxanthin-containing phosphate-buffered saline (Astaxanthin was 3 mM in 0.1 M phosphate-buffered saline) was added at these lipid systems, and resulting two-phase system was sonicated 3 minutes until the mixture homogeneous that did not separate for at least two hours after sonicated. Astaxanthin-SSL were sealed and sterilized. [$^3$H]-astaxanthin and dialyzed method was used to determine the amount of encapsulated astaxanthin. The size of the vesicles was determined by a dynamic light cattering technique. When PG/PC/CHOL were 1:4:5, diameter of liposomes was 20-50 nM (range). Astaxanthin-SSL was very stabilized in at least six months.

So far, many articles reported drug-containing liposomes. However, in general, liposomes are not stabilized. In accordance with this invention, astaxanthin-SSL is very stabilized in at least six months. Therefore astaxanthin-SSL can be used in industry. Astaxanthin-SSL can enhance and improve antioxidant activity of astaxanthin. It is very important that all lipids are extracted from soybean. Therefore it is very safe for human being. Many articles reported lipids, which used for drug-containing liposomes, are syntheses by organic chemistry. However synthetic lipids have some side effects. Methods of preparing of astaxanthin-SSL and phospholipids, which extracted from soybean, are very safe.

Example 6

New Sustained Release Preparation of Astaxanthin

Methods of New Sustained Release Preparation 1 kg polyvinylpyrrolidone (PPD) (molecular weight 40.000) were dissolved in 10 liter of isopropand, and 1 kg of micronized astaxanthin was dispersed in there. 3.5 kg of sugar was placed in suspension and mix. Astaxanthin is coated onto the sugar seed by first combining it with a water soluble system such as polyethylene glycol or polyvinylpyrrolidone.

The resulting astaxanthin coated sugar seeds are then coated with a pharmaceutically acceptable waterinsoluble system such as ethylcellulose, cellulose acetate butyrate or cellulose triacetate, with ethyl cellulose preferred. This coating enables release of the astaxanthin. The average diameter of each of the finished micropellets is about 0.4 to 0.6 mm, preferably about 0.5 mm. This provides a coating with a sufficient amount of channels to enable the astaxanthin to be released. The dissolution rate depends on the weight of the micropellets and solvent system. The pellets were screened.

As desired, the final coated products containing ethyl cellulose coating level of 1% was prepared. The pellets were dried under vacuum. The products contained 99.0% by weight of astaxanthin and 1% by weight ethyl cellulose coating.

Plasma concentration of astaxanthin in sustained preparation is similar as sustained preparation of lutein.

The X-ray diffraction patterns support the fact that astaxanthin and a pharmaceutical acceptable have complex with each other and formed an inclusion complex of them having a structure different from the original structures of the individual components.

The novelty of the present invention indicated in the mixture of the active ingredients with the specified proportions to produce astaxanthin and in the preparation of dosage units are in pharmaceutically acceptable dosage form. The term "pharmaceutical acceptable dosage form" as used hereinabove includes any suitable vehicle for the administration of medications known in the pharmaceutical art, including, by way of example, tablets, capsules, syrups, and elixirs with specified ranges of astaxanthin concentration.

Example 7

Preparation Polymeric Micelles-Astaxanthin

An estimated 40% of approved drugs in the market and nearly 90% of molecules in the developmental pipeline are poorly water-soluble. The challenge to formulate insoluble drugs has met with advent of various insoluble drug formulation technologies. The polymers micelles with both hydrophobic and hydrophilic moiety in the chain can assemble into nano-sized micelles in water. Polymeric micelles solubilize is very important for poorly water-soluble compounds. A major factor in astaxanthin solubilization is the compatibility of astaxanthin and a core of a polymeric micelle. Polymeric micelles may circulate for prolonged periods in blood and gradually release astaxanthin.

Polymeric micelles have gathered considerable attention in the field of astaxanthin and gene delivery due to their excellent biocompatibility, low toxicity, enhanced blood circulation time, and ability to solubilize a large number of astaxanthin in their micellar core. Polymeric micelles have emerged as important pharmaceutical carriers because of their attractive properties. Preparation of polymeric micelles appears to be relatively simple as compared with the other novel drug delivery systems. Polymeric micelles can be easily loaded with a wide variety of poorly soluble drugs, such as astaxanthin, thus resulting in enhance bioavailability of astaxanthin.

The method of Micelle Formation: 200 mg of copolymer were dissolved in 40 ml dimethyl acetamide and the polymer solution was transferred into a pre-swollen membrane and dialyzed against water for 24 h and subsequently lyophilized. The yield of the micelle formation was about 90%.

50 mg of micelle were solubilized by sonication for 40 min in water and stirred for another 3 h. The pH of the solution was adjusted by HCl to pH 2, kept for 14 h and readjusted to pH 7 by NaOH. The solution was again dialyzed against water for 24 h using a pre-swollen membrane to remove the salt and then frozen in liquid nitrogen and lyophilized, resulting in a yield of 90%.

Example 8

Natural Polymers Using in Self-Assembling for Astaxanthin

A. Natural Polymers:

Drug delivery plays an important role in the development of pharmaceutical dosage forms for the healthcare industry because often the duration of the drug release needs to be extended over a period of time. This can be achieved by the incorporation of drugs into polymeric materials to control drug release at a pre-defined and reproducible rate for a prolonged duration.

The majority of the drug delivery systems are fabricated from non-degradable polymers such as silicone, polyurethane and ethylene vinyl acetate copolymers. So far, the polymers were synthesized but chemical polymers have some side effects. Therefore we develop new natural biodegradable polymers. For example, soy polypeptide and sodium Haidai are two natural polymers and they are an abundant, inexpensive and renewable material.

Soy polypeptide (SPP) is isolated from soy protein, which content of 95% (dry basis), was obtained from special soybean (SSB). SSB is natural cultivated and it is not from a transfer-gene seeds. Also, SSBs are cultivated at no pollution area. Natural biodegradable polymer is poly-sodium Haidai (PSH) which extracted from sea-plant Haidai. PSH is cream-colored powder. Molecular weight is about 240000. The major structure is linear polymer.

SPP/PSH is derived from renewable resource. Therefore, using SPP/SH system has good environment value. SPP/PSH has been found good performance as a pervaporation membrane material for the dehydration of ethanol/water mixture. SPP and PSH are biodegradable, environmentally friendly, and readily available from an abundant renewable resource. It had been considered an important material for the development of new materials as devices for biotechnological and biomedical utilization.

B. Self-Assembling Properties

Self-assembling properties were examined by adding water to the liquid block copolymers (10% w/v). The mixture was stirred for 10 min. Micelle formation was determined at 25° C.

Measurement of astaxanthin solubility in 10% w/v diblock copolymer micelles: The maximum astaxanthin solubility in micelles was determined as follows: In a glass flask, 0.5 g of copolymer and 0.1 to 0.15 g of astaxanthin was weighed and then mixed at 50° C. for 10 min using a magnetic stirrer followed by addition of 5 ml of filtered water (0.1 μm Millipore). The solution was stirred for 24 h at room temperature and then filtered through a 0.1 μm Millipore filter to remove non-solubilized astaxanthin. A product was obtained using an ultraviolet (UV) spectrophotometer. Absorbances were measured at 260 nm at 233 nm. Solubility data are an average of at least three measurements.

The SPP/PSH systems are as a good astaxanthin carrier, polymer micelle possesses the following advantages: good stability, increasing solubility of insoluble drugs, release slowly, improving drug bioavailability.

Example 9

Preparation of Lutein Plus Astaxanthin-Containing Sterically Stabilized Liposomes Hydrogenated phosphatidylcholine (PC), phosphatidylglycerol (PGL), and phosphatidylserine (PS) were extracted from soybean. All above lipids were finally purified on silicic acid columns, shown to be pure by thin-layer chromatography and stored in chloroform in sealed ampules under nitrogen until use. Phospholipids mixed with cholesterol (CHOL) and long-chain alcohol. The solvent was removed under reduced pressure by a rotory evaporator. Lipids were redissolved in the organic phase and reversed phase will be formed. Lutein plus astaxanthin (50%:50%)-containing phosphate-buffered saline (Lutein plus astaxanthin was 3 mM in 0.1 M phosphate-buffered saline) was added at these lipid systems, and resulting two-phase system was sonicated 3 minutes until the mixture homogeneous that did not separate for at least two hours after sonicated. Lutein plus astaxanthin-SSL were sealed and sterilized. [$^3$H]-lutein plus astaxanthin and dialyzed method was used to determine the amount of encapsulated lutein plus astaxanthin. The size of the vesicles was determined by a dynamic light cattering technique. When PG/PC/CHOL were 1:4:5, diameter of liposomes was 20-50 nM (range). Lutein plus astaxanthin-SSL was very stabilized in at least six months.

So far, many articles reported drug-containing liposomes. However, in general, liposomes are not stabilized. In accordance with this invention, lutein plus astaxanthin-SSL is very stabilized in at least six months. Therefore lutein plus astaxanthin-SSL can be used in industry. Lutein plus astaxanthin-SSL can enhance and improve antioxidant activity of lutein plus astaxanthin. It is very important that all lipids are extracted from soybean. Therefore it is very safe for human being. Many articles reported lipids, which used for drug-containing liposomes, are syntheses by organic chemistry. However synthetic lipids have some side effects. Methods of preparing of lutein plus astaxanthin-SSL and phospholipids, which extracted from soybean, are very safe.

Example 10

New Sustained Release Preparation of Lutein Plus Astaxanthin

Methods of New Sustained Release Preparation 1 kg polyvinylpyrrolidone (PPD) (molecular weight 40.000) were dissolved in 10 liter of isopropand, and 1 kg of micronized lutein plus astaxanthin was dispersed in there. 3.5 kg of sugar was placed in suspension and mix. Lutein plus astaxanthin (50%:50%) is coated onto the sugar seed by first combining it with a water soluble system such as polyethylene glycol or polyvinylpyrrolidone.

The resulting lutein plus astaxanthin coated sugar seeds are then coated with a pharmaceutically acceptable water-insoluble system such as ethyl cellulose, cellulose acetate butyrate or cellulose triacetate, with ethyl cellulose preferred. This coating enables release of the lutein plus astaxanthin. The average diameter of each of the finished micropellets is about 0.4 to 0.6 mm, preferably about 0.5 mm. This provides a coating with a sufficient amount of channels to enable the lutein plus astaxanthin to be released. The dissolution rate depends on the weight of the micropellets and solvent system. The pellets were screened.

As desired, the final coated products containing ethyl cellulose coating level of 1% was prepared. The pellets were dried under vacuum. The products contained 99.0% by weight of lutein plus astaxanthin and 1% by weight ethyl cellulose coating.

Plasma concentration of lutein plus astaxanthin is similar as sustained preparation of lutein The X-ray diffraction patterns support the fact that lutein plus astaxanthin and a pharmaceutical acceptable have complex with each other and formed an inclusion complex of them having a structure different from the original structures of the individual components.

The novelty of the present invention indicated in the mixture of the active ingredients with the specified proportions to produce lutein plus astaxanthin and in the preparation of dosage units are in pharmaceutically acceptable dosage form. The term "pharmaceutical acceptable dosage form" as used hereinabove includes any suitable vehicle for the administration of medications known in the pharmaceutical art, including, by way of example, tablets, capsules, syrups, and elixirs with specified ranges of lutein plus astaxanthin concentration.

Example 11

Preparation Polymeric Micelles-Lutein Plus Astaxanthin

An estimated 40% of approved drugs in the market and nearly 90% of molecules in the developmental pipeline are poorly water-soluble. The challenge to formulate insoluble drugs has met with advent of various insoluble drug formulation technologies. The polymers micelles with both hydrophobic and hydrophilic moiety in the chain can assemble into nano-sized micelles in water. Polymeric micelles solubilize is very important for poorly water-soluble compounds. A major factor in lutein plus astaxanthin (50%:50%) solubilization is the compatibility of lutein plus astaxanthin and a core of a polymeric micelle. Polymeric micelles may circulate for prolonged periods in blood and gradually release lutein plus astaxanthin.

Polymeric micelles have gathered considerable attention in the field of lutein plus astaxanthin and gene delivery due to their excellent biocompatibility, low toxicity, enhanced blood circulation time, and ability to solubilize a large number of lutein, plus astaxanthin in their micelle core. Polymeric micelles have emerged as important pharmaceutical carriers because of their attractive properties. Preparation of polymeric micelles appears to be relatively simple as compared with the other novel drug delivery systems. Polymeric micelles can be easily loaded with a wide variety of poorly soluble drugs, such as lutein plus astaxanthin, thus resulting in enhance bioavailability of lutein plus astaxanthin.

The method of Micelle Formation: 200 mg of copolymer were dissolved in 40 ml dimethyl acetamide and the polymer solution was transferred into a pre-swollen membrane and dialyzed against water for 24 h and subsequently lyophilized. The yield of the micelle formation was about 90%.

50 mg of micelle were solubilized by sonication for 40 min in water and stirred for another 3 h. The pH of the solution was adjusted by HCl to pH 2, kept for 14 h and readjusted to pH 7 by NaOH. The solution was again dialyzed against water for 24 h using a pre-swollen membrane to remove the salt and then frozen in liquid nitrogen and lyophilized, resulting in a yield of 90%.

Example 12

Natural Polymers Using in Self-Assembling for Lutein Plus Astaxanthin

A. Natural Polymers:

Drug delivery plays an important role in the development of pharmaceutical dosage forms for the healthcare industry because often the duration of the drug release needs to be extended over a period of time. This can be achieved by the incorporation of drugs into polymeric materials to control drug release at a pre-defined and reproducible rate for a prolonged duration.

The majority of the drug delivery systems are fabricated from non-degradable polymers such as silicone, polyurethane and ethylene vinyl acetate copolymers. So far, the polymers were synthesized but chemical polymers have some side effects. Therefore we develop new natural biodegradable polymers. For example, soy polypeptide and polymers sodium Haidai are two natural polymers and they are an abundant, inexpensive and renewable material.

Soy polypeptide (SPP) is isolated from soy protein, which content of 95% (dry basis), was obtained from special soybean (SSB). SSB is natural cultivated and it is not from a transfer-gene seeds. Also, SSBs are cultivated at no pollution area. Natural biodegradable polymer is poly-sodium Haidai (PSH) is extracted from sea plant Haidai. PSH is cream-colored powder. Molecular weight is about 240000. The major structure is linear polymer.

SPP/PSH is derived from renewable resource. Therefore, using SPP/PSH system has good environment value. SPP/PSH has been found good performance as a pervaporation membrane material for the dehydration of ethanol/water mixture. SPP and PSH are biodegradable, environmentally friendly, and readily available from an abundant renewable resource. It had been considered an important material for the development of new materials as devices for biotechnological and biomedical utilization.

B. Self-Assembling Properties

Self-assembling properties were examined by adding water to the liquid block copolymers (10% w/v). The mixture was stirred for 10 min. Micelle formation was determined at 25° C.

Measurement of lutein plus astaxanthin solubility in 10% w/v diblock copolymer micelles: The maximum lutein plus astaxanthin solubility in micelles was determined as follows: In a glass flask, 0.5 g of copolymer and 0.1 to 0.15 g of lutein plus astaxanthin was weighed and then mixed at 50° C. for 10 min using a magnetic stirrer followed by addition of 5 ml of filtered water (0.1 μm Millipore). The solution was stirred for 24 h at room temperature and then filtered through a 0.1 μm Millipore filter to remove non-solubilized lutein plus astaxanthin. A product was obtained using an ultraviolet (UV) spectrophotometer. Absorbances were measured at 260 nm at 233 nm. Solubility data are an average of at least three measurements.

The SPP/PSH systems are as a good lutein plus astaxanthin carrier, polymer micelle possesses the following advantages: good stability, increasing solubility of insoluble drugs, release slowly, improving drug bioavailability.

Example 13

Pharmaceutical Characters of New Preparation

The method for detecting described as below:

Chickens (50), weighing 1.0±0.2 kg, were randomly divided into two treatments, with 25 chickens each. Chickens were individually housed in cages measuring 0.2×0.2 m, and were submitted to a lighting program of 16 h light/day. Chickens were kept under a temperature of 20±5° C. Feed and water were supplied ad libitum.

After two weeks of washout period, when the chickens were fed lutein or preparation of lutein with basal diet, two groups were fed the basal diets lutein or preparation of lutein for a period of 15 days. Lutein contents were determined using a HPLC method. The basal diet contained 0.5 mg lutein/kg. The two diets were formulated to contain the same level of 15 mg lutein/kg. All feeds were prepared every day.

Morning blood samples were taken on day 0, and days 3, 6, 12 for lutein analysis. The number of eggs laid by each chicken was counted during the experiment. Blood samples were obtained by puncture of the vena ulnaris. One milliliter of blood was sampled from each chicken. The plasma was separated by centrifugation. Plasma lutein concentrations have been detected.

Plasma samples were centrifuged at 1040×g for 5 mm to remove fibrous debris. 150 L of a mixture of internal standards added to 150 pL of plasma. Hexane was added to this mixture and the contents of the tubes were vortex-mixed. Precipitated proteins were removed by centrifugation (1040×g, 5 mm) at room temperature. Aliquots of the organic phase were removed from each sample and the solvent was evaporated under nitrogen. One aliquot from each sample was dissolved in methanol.

A single gradient-type HPLC system was used for the parallel analysis of plasma concentration of lutein. The HPLC systems consisted of two solvent-delivery systems detected with a 436-nm and a 280-nm filter. The samples were analyzed by HPLC method. Lutein was quantified by determining the peak area at 445 nm.

The experiments were designed as completely randomized and all statements of significance were based on probability $p<0.05$.

| Plasma lutein concentration (μg lutein/ml) | | | |
|---|---|---|---|
| Lutein | A | B | C |
| 1.20 ± 0.10 | 2.6 ± 0.15 | 2.3 ± 0.20 | 2.85 ± 0.21 |

A: Lutein-SSL group;
B: Lutein-sustained group;
C: Lutein-preparation of polymeric micelles The results showed that lutein in serum of all three preparations were significantly higher than lutein control group. The polymeric micelles group is higher than lutein-SSL group and lutein-sustained group. Lutein-SSL group is higher than lutein-sustained group.

The results indicated that new preparation of lutein can significantly increase bioavailability of lutein.

It will thus be shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letter Patent is set forth in the appended claims:

1. A pharmaceutical preparation for increasing bioavailability and solubility of lutein, comprising an effective amount of polymeric micelles containing lutein, which have been made by self-assembling soy polypeptide and Hadai extract having a molecular weight of about 240,000 and dehydrating in an ethanol/water mixture.

* * * * *